US006420620B1

(12) United States Patent
De Bie et al.

(10) Patent No.: US 6,420,620 B1
(45) Date of Patent: Jul. 16, 2002

(54) PROCESS FOR PREPARING STYRENES

(75) Inventors: Johan Hendrik De Bie; Hendrik Dirkzwager, both of Amsterdam; Robertus Raymundus Maria Overtoom, Moerdijk; Marinus Van Zwienen, Amsterdam, all of (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/622,276

(22) PCT Filed: Feb. 16, 1999

(86) PCT No.: PCT/EP99/01006

§ 371 (c)(1),
(2), (4) Date: Aug. 14, 2000

(87) PCT Pub. No.: WO99/42426

PCT Pub. Date: Aug. 26, 1999

(30) Foreign Application Priority Data

Feb. 17, 1998 (EP) .............................. 98200493

(51) Int. Cl.⁷ .............................. C07C 1/20; C07C 1/24
(52) U.S. Cl. ...................... 585/437; 585/435; 585/436; 585/319
(58) Field of Search ................ 585/435, 436, 585/437, 319

(56) References Cited

U.S. PATENT DOCUMENTS

| 2,929,855 A | * | 3/1960 | O'Conner et al. | 585/435 |
| 3,351,635 A | * | 11/1967 | Kollar | 585/435 |
| 3,442,963 A | * | 5/1969 | Korchak | 585/435 |
| 3,526,674 A | * | 9/1970 | Becker et al. | 585/435 |
| 3,658,928 A | * | 4/1972 | Skinner et al. | 585/437 |
| 4,250,344 A | * | 2/1981 | Sherwin et al. | 585/437 |
| 4,273,622 A | | 6/1981 | Becker | |
| 4,375,570 A | | 3/1983 | Yudovich | |
| 5,210,354 A | * | 5/1993 | Dubner et al. | 585/435 |
| 5,276,235 A | * | 1/1994 | Dubner | 585/435 |
| 5,639,928 A | * | 6/1997 | Dubner et al. | 585/435 |

OTHER PUBLICATIONS

Search Report dated Jun. 14, 1999.

* cited by examiner

Primary Examiner—Walter D. Griffin

(57) ABSTRACT

A process for the preparation of styrene or substituted styrenes that includes the steps of: subjecting a feed containing 1-phenyl ethanol or substituted 1-phenyl ethanol to a dehydration treatment in the presence of a dehydration catalyst; subjecting the resulting product stream to a separation treatment, thus obtaining a stream containing styrene or substituted styrene and a residual fraction containing heavy ends; and converting at least part of these heavy ends to styrene or substituted styrenes by subjecting a stream containing these heavy ends to a cracking treatment in the presence of an acidic cracking catalyst.

13 Claims, No Drawings

PROCESS FOR PREPARING STYRENES

The present invention relates to a process for the preparation of styrene or substituted styrenes from a feed containing 1-phenyl ethanol (also known as α-phenyl ethanol or methyl phenyl carbinol) or substituted 1-phenyl ethanol, involving the conversion of bis(phenyl ethyl)ethers or substituted bis(phenyl ethyl)ethers into styrene or substituted styrenes. The present invention also relates to the conversion per se of bis(phenyl ethyl)ethers or substituted bis(phenyl ethyl)ethers into styrene or substituted styrenes.

A commonly known method for manufacturing styrene is the coproduction of propylene oxide and styrene starting from ethylbenzene. In general such process involves the steps of (i) reacting ethylbenzene with oxygen or air to form ethylbenzene hydroperoxide, (ii) reacting the ethylbenzene hydroperoxide thus obtained with propene in the presence of an epoxidation catalyst to yield propylene oxide and 1-phenyl ethanol, and (iii) converting the 1-phenyl ethanol into styrene by dehydration using a suitable dehydration catalyst. The present invention particularly focuses on the last step, i.e. the dehydration of 1-phenyl ethanol to yield styrene.

During the dehydration of 1-phenyl ethanol to styrene several by-products in addition to water are formed, such as polystyrenes including dimers and trimers of styrene and bis(phenyl ethyl)ethers. A major part of the bis(phenyl ethyl)ethers formed consists of bis(α,α-phenyl ethyl)ether, which is assumed to result from the reaction between two molecules of 1-phenyl ethanol. Another bis(phenyl ethyl) ether normally formed in a substantial amount is bis(α,β-phenyl ethyl)ether. Bis(β,β-phenyl ethyl)ether is normally formed in minor amounts. The latter two bis(phenyl ethyl) ethers are assumed to result from the reaction between 1- and 2-phenyl ethanol and from the reaction between two molecules of 2-phenyl ethanol, respectively. The 2-phenyl ethanol is usually already present in small amounts in the feed to the dehydration treatment. This is predominantly the result of the preceding epoxidation step, wherein beside the main products propylene oxide and 1-phenyl ethanol also some 2-phenyl ethanol and methyl phenyl ketone are formed. Also in the oxidation step some 2-phenyl ethanol and methyl phenyl ketone is already formed. Since the boiling points of 1- and 2-phenyl ethanol and methyl phenyl ketone are all very close, a distillation treatment will not effect full separation.

The bis(phenyl ethyl)ethers together form a substantial part of the so called residual fraction or heavy ends, i.e. all components present in a stream having a boiling point which is higher than the boiling point of 1-phenyl ethanol. Normally the heavy ends will contain 5 to 50% by weight of bis(phenyl ethyl)ethers, suitably 10 to 40% by weight. As stated herein before, a substantial part of the bis(phenyl ethyl)ethers is composed of bis(α,α-phenyl ethyl)ether. The remaining part is composed of bis(α,β-phenyl ethyl)ether with small amounts of bis(β,β-phenyl ethyl)ether being sometimes present as well. Other main components present in the heavy ends include 2-phenyl ethanol (0–40% by weight), 1-phenyl ethanol (0–20% by weight), methyl phenyl ketone (0–30% by weight) and polystyrenes (0–40% by weight). Small quantities of other ethers, such as the ether reaction product of 1-phenyl ethanol and phenol, may also be present. The exact quantities of each of these components is determined by the specific reaction conditions and catalyst employed in the dehydration step as well as by the product separation means applied after this dehydration step. Beside these main components the remainder of the heavy ends, up to 100% by weight, is formed by other compounds having a boiling point higher than that of 1-phenyl ethanol.

In the conventional processes for manufacturing styrene the heavy ends formed in the course of the process are disposed of as fuel and are burnt in a boiler house. In this way relatively valuable products are lost. It would be beneficial if the amount of valuable products present in the heavy ends could be reduced.

The present invention aims to provide an effective process for converting components present in the heavy ends into styrene, thus increasing the overall yield of styrene while lowering the amount of heavy ends.

In U.S. Pat. No. 4,375,570 a process for the recovery of aromatic hydrocarbons from dehydration residues obtained in the preparation of styrene from 1-phenyl ethanol is disclosed. The process involves subjecting the dehydration residues to a thermal cracking treatment at a temperature in the range of 325 to 475° C. and at an elevated pressure of about 5 to 21 bar, withdrawing the cracked effluent from the reaction zone and recovering liquid aromatic hydrocarbons from this cracked effluent. The dehydration residue generally is the residual fraction obtained after removal of the crude styrene from the dehydration product stream. It was found that by carrying out the thermal cracking at elevated pressure, the $C_8$ aromatic hydrocarbons formed were composed predominantly of ethylbenzene and contained low amounts (usually less than 3% by weight) of styrene monomer. The ethylbenzene can be recycled to the oxidation step where ethylbenzene hydroperoxide is formed, which is a precursor of 1-phenyl ethanol from which styrene is formed. Thus, the overall styrene selectivity of the process is increased and the amount of heavy ends eventually obtained is decreased. The thermal cracking treatment, however, requires rather severe conditions, as a result of which tar-like products are formed which in return result in fouling of the equipment. Furthermore, these severe conditions are less desired for reasons of process control and necessitate the use of more expensive equipment. Moreover, the improvement of overall styrene selectivity and yield is obtained indirectly, i.e. via the production of ethylbenzene. During the conversion of ethylbenzene into styrene additional losses again occur.

The present invention has the advantage that it provides a process wherein the improvement of styrene selectivity and styrene yield is obtained more directly. Furthermore, the process of the present invention does not involve any thermal cracking treatment requiring rather severe process conditions, but makes use of a less severe treatment to enhance styrene selectivity and overall styrene yield.

Accordingly, the present invention relates to a process for the preparation of styrene or substituted styrenes comprising the steps of:

(a) subjecting a feed containing 1-phenyl ethanol or substituted 1-phenyl ethanol to a dehydration treatment in the presence of a suitable dehydration catalyst, (b) subjecting the resulting product stream to a separation treatment, thus obtaining a stream containing styrene or substituted styrene and a residual fraction containing heavy ends, and (c) converting at least part of these heavy ends to styrene or substituted styrenes by subjecting a stream containing these heavy ends to a cracking treatment in the presence of an acidic cracking catalyst.

Within the further context of the present application the term "styrene" also embraces substituted styrenes, by which are meant styrenes containing one or more substituents bonded to the aromatic ring or to the vinyl group. Such substituents typically include alkyl groups, such as methyl or ethyl groups. Similarly, the terms "bis(phenyl ethyl) ethers" and "1-phenyl ethanol" also embrace respectively substituted bis(phenyl ethyl)ethers and substituted 1-phenyl ethanols having the same substituents as the corresponding substituted styrenes.

The production of styrene by dehydrating 1-phenyl ethanol is well known in the art. It can be carried out both in the gas phase and in the liquid phase. Suitable dehydration catalysts include for instance acidic materials like alumina, alkali alumina, aluminium silicates and H-type synthetic zeolites. Dehydration conditions are also well known and usually include reaction temperatures of 100–200° C. for liquid phase dehydration and 210–320° C., typically 280–310° C., for gas phase dehydration. Pressures usually range from 0.1 to 10 bar. In principle any known dehydration process can be applied in step (a) of the process according to the present invention. For the purpose of the present invention gas phase dehydration is preferred. In a preferred embodiment the gas phase dehydration is carried out at a temperature in the range of 230 to 280° C. using an alumina-based dehydration catalyst. It has been found advantageous to apply these relatively low temperatures for gas phase dehydration so as to promote the formation of bis(phenyl ethyl)ethers and to limit the formation of other high boiling components like polystyrenes. The latter will add to the heavy ends from which no valuable products can be obtained. The increased amount of bis(phenyl ethyl) ethers formed at the lower reaction temperatures can then be converted into styrene in step (c). As a result, the overall styrene selectivity and yield are increased.

The feed containing 1-phenyl ethanol used in step (a) of the present process is suitably obtained from a preceding epoxidation step, wherein optionally substituted ethyl benzene hydroperoxide is reacted with propene to yield propylene oxide and 1-phenyl ethanol or substituted 1-phenyl ethanol. In such epoxidation step a homogeneous catalyst or a heterogeneous catalyst can be applied. As homogeneous catalysts molybdenum compounds are frequently applied, while catalysts based on titanium on a silica carrier are often used as heterogeneous catalysts. Conditions under which epoxidation is carried out are known in the art and include temperatures of 75 to 150° C. and pressures up to 80 bar with the reaction medium being in the liquid phase. The effluent from the epoxidation step is normally first subjected to a separation treatment to remove the propylene oxide formed, after which the residual stream, containing 1-phenyl ethanol, is suitably subjected to one or more further separation treatments, inter alia to remove ethyl benzene for reuse in an earlier stage of the process.

Step (b) of the present process comprises subjecting the product stream, which results from step (a) and which inter alia contains the styrene monomer formed, to a separation treatment. The styrene-rich fraction, which also contains the dehydration water, will be removed as the top fraction, whilst a residual fraction containing heavy ends formed during the dehydration will be obtained as the bottom fraction. Such separation can be effected in several ways, but most suitably is achieved by flashing or distillation. It has been found particularly advantageous within the framework of the present invention to first subject the residual fraction obtained in step (b) to a separation treatment to remove methyl phenyl ketone (or substituted methyl phenyl ketone as may be the case) before subjecting it to the cracking treatment in step (c). Such separation treatment can be carried out in any known manner and suitably involves a flashing or distillation treatment.

In a further preferred embodiment of the present invention the residual fraction obtained in step (b) is first subjected to a separation treatment to remove methyl phenyl ketone, after which the remaining fraction is subjected to a further separation treatment together with the above described effluent from the preceding epoxidation step to remove 1-phenyl ethanol. As indicated above, propylene oxide and suitably also ethyl benzene have been removed from said epoxidation effluent prior to it being subjected to the separation treatment for removing 1-phenyl ethanol. Thereafter cracking is carried out.

The conditions under which the cracking step is performed may vary within wide limits. Suitably the cracking temperature may range from 150° C. to 325° C., but preferably the cracking temperature is from 180 to 260° C., whilst the weight hourly space velocity suitably has a value in the range of from 0.5 to 10 kg fresh feed per kg catalyst per hour. Accordingly, any recycled part of the feed stream is not included in this figure. When included, the weight hourly space velocity consequently may have a higher value than the range indicated. The pressure applied may have any practically applicable value, but preferably the pressure is from 0.1 to 5 bar. Most preferably, the pressure is substantially atmospheric.

The cracking catalyst used must be acidic, or at least have an acidic outer surface, in order to have sufficient cracking activity. The catalyst used may be either heterogeneous or homogeneous. Suitable heterogeneous acidic cracking catalysts then include aluminosilicates like the synthetic zeolites, examples of which are ZSM-5 and H-ZSM-5, as well as amorphous inorganic oxide materials like alumina and silica-alumina. It has, however, been found particularly advantageous to employ a cracking catalyst comprising amorphous silica-alumina. In principle any amorphous silica-alumina having sufficient acidity to catalyse cracking of the bis(phenyl ethyl)ethers into styrene may be used. The amorphous silica-alumina used, however, suitably has an alumina content in the range of from 5 to 75% by weight, preferably 35 to 70% by weight. In addition to the silica-alumina, a binder material may be present. Typical binder materials are inorganic oxides, such as silica, alumina, boria, titania and zirconia. Of these, alumina is preferred. If used at all, the binder is used in amounts varying from 10 to 90% by weight, preferably 20 to 80% by weight, based on total weight of catalyst. The total pore volume of the cracking catalyst suitably ranges from 0.3 to 1.5 ml/g (as determined by mercury intrusion porosimetry, ASTM D 4282-88), more preferably 0.4 to 1.2 ml/g, whilst its surface area suitably is at least 150 $m^2/g$, more suitably from 175 to 600 $m^2/g$ and most suitably 185 to 450 $m^2/g$.

In case a heterogeneous catalyst is used the cracking operation can be performed in different ways known in the art. The cracking operation can, for instance, be operated in a fixed bed mode, where the feed is led over a bed of cracking catalyst particles. In this case the feed can be passed through the catalyst bed either downwardly or upwardly. Alternatively, the cracking operation can be carried out in a trickle bed mode. In such mode of operation the feed enters the reactor at the top section and is trickled over the catalyst bed. The product section is subsequently withdrawn at the bottom section of the reactor. Still another option is to perform the cracking operation in a slurry type of operation by adding small catalyst particles to the feed stream, while styrene is removed overhead as vapour. For the purpose of the present invention it has been found particularly advantageous to apply the trickle bed cracking operation.

If used in a fixed bed or trickle bed mode, the catalyst may have any shape and size conventionally applied in these types of operation. Accordingly, the catalyst particles may be in the form of spheres, trilobes, quadrulobes, cylinders and the like. Their size may vary within the normal commercially useful limits.

Suitable homogeneous catalysts are those acidic catalysts which are dispersible or soluble in the cracking reaction medium. Examples of suitable homogeneous catalysts are p-toluene sulphonic acid and sulphuric acid. Of these, the use of para-toluene sulphonic acid is preferred.

The present invention also relates to a process for converting bis(phenyl ethyl)ethers into styrene or substituted styrene, which process comprises contacting the bis(phenyl ethyl)ethers with a catalyst comprising amorphous silica-alumina at elevated temperature.

The catalyst comprising amorphous silica-alumina is the same as described herein before. The cracking conditions are also the same as described herein before. The bis(phenyl ethyl)ethers-containing feed may contain other constituents beside the bis(phenyl ethyl)ethers. The nature of these constituents depends on the origin of the feed. If the feed for instance is a stream originating from a process wherein styrene is manufactured from 1-phenyl ethanol such constituents may include polystyrenes, methyl phenyl ketone, 1- and 2-phenyl ethanol and other high boiling components. The exact composition of the feed in that case also depends on the specific location in the process where the cracking operation is incorporated.

The invention is further illustrated by the following examples without restricting its scope to these particular embodiments.

EXAMPLE 1

A cracking experiment was performed in a trickle phase reactor set-up consisting of fixed bed, feed supply pump, gas/liquid product separator and liquid recycle pump facilities.

The fixed bed was operated in trickle phase mode and contained 50 grams of an amorphous silica-alumina (ASA) 3.5 mm trilobe catalyst (silica/alumina ratio 45/55; pore volume 0.72 ml/g; surface area 219 m$^2$/g). The trickle phase reactor was operated at typical reaction conditions of 190–225° C. and 1 bar pressure.

In this experiment the feed stream to the trickle phase reactor consisted apart from polystyrene derivatives and other heavy boiling components of 5.8% w bis($\alpha,\alpha$-phenyl ethyl)ether and 20.3% w bis($\alpha,\beta$-phenyl ethyl)ether. The feed stream represented a typical product stream of the 1-phenyl ethanol dehydration process carried out in a styrene reactor of a commercial Styrene Monomer/Propylene Oxide plant, from which product stream methyl phenyl ketone, styrene and water were removed by distillation.

The feed stream was added to the top of the reactor at a rate of 50 grams/hour. Prior to introduction the feed stream to the reactor it was mixed with approximately 5 grams/hour of steam and 100 grams/hour of liquid recycle stream. The outlet stream of the reactor was led to a gas/liquid separator operated at approximately 200° C. The gas stream leaving the gas/liquid separator, approximately 30 grams/hour, contained the low boiling reaction products like styrene and water, which were collected and weighed after condensation. The liquid stream leaving the gas separator was partly recycled to the top of the reactor at a rate of 100 grams/hour and partly removed as a bleed stream at a rate of approximately 20 grams/hour. The experimental run was started at 190° C. and during the course of the experiment temperature was increased to 225° C. to compensate for some decline in catalytic activity. Conversion of bis($\alpha,\alpha$-phenyl ethyl)ether and bis($\alpha,\beta$-phenyl ethyl)ether, as measured throughout the experimental run, amounted to approximately 80% and 60% respectively. Before the experimental run was stopped after 792 hours at an end temperature of 225° C., a sample was taken from the recycle bleed stream and this sample was analysed by means of gaschromatographic analysis for the contents of bis($\alpha,\alpha$-phenyl ethyl)ether and bis($\alpha,\beta$-phenyl ethyl)ether.

It was found that the conversion figures for bis($\alpha,\alpha$-phenyl ethyl) ether and bis($\alpha,\beta$-phenyl ethyl)ether were 81.9% and 70.0%, respectively. This means that 81.9% of the bis($\alpha,\alpha$-phenyl ethyl)ether present in the feed stream and 70.0% of the bis($\alpha,\beta$-phenyl ethyl)ether present in the feed stream were converted. It was further found that the yield of styrene and styrene precursors (such as 1-phenyl ethanol and 2-phenyl ethanol) amounted to 15.7%w on the basis of heavy ends intake flow.

EXAMPLE 2

The experiment was performed batchwise in a 1 liter glass reactor equipped with heating mantle and product vapour condensing facilities. Reaction products were collected overhead by condensation, weighed and analysed for styrene content. The experiment was performed at atmospheric pressure with the same feedstock and catalyst as described in example 1, although the catalyst was used in powder form dispersed in the feed stream in stead of in a fixed bed.

The reactor was loaded with 190 grams of feedstock and 3.8 grams of catalyst powder at room temperature. The reactor was heated at a rate of 2° C. per minute to an end temperature of 250° C. At this temperature the cracking reaction was allowed to continue for another 2 hours. From gaschromatographic analyses of the residue and the starting feedstock it was calculated that the conversions of bis($\alpha,\alpha$-phenylethylether) and bis($\alpha,\beta$-phenylethylether) amounted to 100% and 99.5%, respectively. The yield of styrene and styrene precursors amounted to 20.0%w on the basis of reactor intake.

COMPARATIVE EXAMPLE 1

A similar experiment was performed under the same experimental conditions as described in Example 2, except that a typical commercially available Aluminium Oxide (Al$_2$O$_3$) powder was used as catalyst, which may suitably be applied in 1-phenyl ethanol dehydration reaction. From gaschromatographic analyses of the residue and the starting feedstock, conversions of bis($\alpha,\alpha$-phenyl ethyl) ether and bis($\alpha,\beta$-phenyl ethyl)ether of 0.5% and 7.4%, respectively, were calculated.

The low conversions obtained illustrate the beneficial effects of using ASA as heterogeneous catalyst in stead of conventional aluminium oxide catalyst.

EXAMPLE 3

In this example para-toluene sulphonic acid (pTSA) was used as homogeneous catalyst. A sample of heavy boiling liquids normally applied as bleedstream of the commercial Styrene Monomer/Propylene Oxide plant was used as high boiling feedstock. This feedstock contains high boiling products made both in the Styrene reaction section and in the preceding oxidation and epoxidation reaction sections.

The benchscale unit consisted of a 500 ml glass vessel, electrically heated externally, in which the reactants were mixed by means of a magnetic stirrer. The contents of the vessel were circulated via a loop, in which fresh feed and pTSA were injected, and a residue was removed from the system. Circulation rate was approximately a factor of 20 higher than the fresh feed rate. The liquid level of the reactor was controlled in order to keep the residence time constant. The reactor was operated at atmospheric pressure and at a temperature varying between 200° C. and 230° C. The volatile products were removed overhead, condensed and collected. A cooling medium of −20° C. to 0° C. was used for this purpose. At a feed rate of 110 grams/hour, a temperature of 230° C., a residence time of 1.0 hours and 1.73 grams/hour of pTSA dosing rate, the yield of styrene and styrene precursor was found to be 14.8%w of total heavy ends reactor intake flow.

What is claimed is:

1. Process for the preparation of styrene or substituted styrenes comprising the steps of:
   (a) subjecting a feed containing 1-phenyl ethanol or substituted 1-phenyl ethanol to a dehydration treatment in the presence of a dehydration catalyst;
   (b) subjecting the resulting product stream to a separation treatment, thus obtaining a stream containing styrene or substituted styrene and a residual fraction containing heavy ends; and
   (c) converting at least part of these heavy ends to styrene or substituted styrenes by subjecting a stream containing these heavy ends to a cracking treatment in the presence of an acidic cracking catalyst.

2. Process according to claim 1, wherein the 1-phenyl ethanol or substituted 1-phenyl ethanol used in step (a) is obtained from a preceding epoxidation step, wherein optionally substituted ethyl benzene hydroperoxide is reacted with propene to yield propylene oxide and 1-phenyl ethanol or substituted 1-phenyl ethanol.

3. Process according to claim 1, wherein step (a) is carried out at a temperature in the range of 230 to 280° C. using an alumina-based dehydration catalyst.

4. Process according to claim 1, wherein the residual fraction obtained in step (b) is first subjected to a separation treatment to remove methyl phenyl ketone or substituted methyl phenyl ketone before being subjected to the cracking treatment in step (c).

5. Process according to claim 2, wherein the residual fraction obtained in step (b) is first subjected to a separation treatment to remove methyl phenyl ketone or substituted methyl phenyl ketone and to a further separation treatment together with an effluent from the preceding epoxidation step to remove 1-phenyl ethanol or substituted 1-phenyl ethanol before the residual fraction thus obtained is subjected to the cracking treatment in step (c).

6. Process according to claim 4, wherein cracking step (c), is carried out at a temperature in the range of from 180 to 260° C. and at a weight hourly space velocity in the range of from 0.5 to 10 kg/kg.h.

7. Process according to claim 4, wherein the acidic cracking catalyst used in step (c) is a heterogeneous cracking catalyst, comprising amorphous silica-alumina.

8. Process according to claim 4, wherein the acidic cracking catalyst used in step (c) is a homogeneous cracking catalyst, comprising p-toluene sulphonic acid.

9. Process according to any one of claims 1 to 6, wherein the acidic cracking catalyst used in step (c) is a homogeneous cracking catalyst.

10. Process according to claim 9, wherein the homogeneous cracking catalyst comprises p-toluene sulphonic acid.

11. Process for converting bis(phenyl ethyl)ethers into styrene or substituted styrene, which process comprises contacting the bis(phenyl ethyl)ethers with a catalyst comprising amorphous silica-alumina at a temperature in the range of from 150 to 325° C.

12. Process according to claim 11, wherein the catalyst has a total pore volume of 0.3 to 1.5 ml/g and a surface area of at least 150 $m^2$/g.

13. Process according to claim 11, wherein the catalyst has a total pore volume of 0.3 to 1.5 ml/g and a surface area from 175 to 600 $m^2$/g.

* * * * *